United States Patent [19]
Winslow et al.

[11] Patent Number: 6,083,225
[45] Date of Patent: Jul. 4, 2000

[54] METHOD AND INSTRUMENTATION FOR IMPLANT INSERTION

[75] Inventors: Charles J. Winslow, Walnut Creek; Steven T. Mitchell, Pleasant Hill; Kirk Jayne, Alameda, all of Calif.; Charles D. Ray, Williamsburg, Va.

[73] Assignee: Surgical Dynamics, Inc., Norwalk, Conn.

[21] Appl. No.: 08/889,661

[22] Filed: Jul. 8, 1997

Related U.S. Application Data

[63] Continuation of application No. 08/615,379, Mar. 14, 1996, abandoned.

[51] Int. Cl.⁷ .................................................. A61B 17/56
[52] U.S. Cl. ................................ 606/61; 606/99; 623/17
[58] Field of Search .................................. 606/61, 80, 90, 606/99; 623/17; D24/135

[56] References Cited

U.S. PATENT DOCUMENTS

| | | | |
|---|---|---|---|
| D. 374,283 | 10/1996 | Michelson | D24/135 |
| D. 397,436 | 8/1998 | Michelson | D24/135 |
| 3,486,505 | 12/1969 | Morrison | 606/90 |
| 3,848,601 | 11/1974 | Ma et al. . | |
| 3,867,932 | 2/1975 | Huene | 606/80 |
| 3,916,907 | 11/1975 | Peterson . | |
| 4,059,115 | 11/1977 | Junashev et al. . | |
| 4,328,593 | 5/1982 | Sutter et al. . | |
| 4,501,269 | 2/1985 | Bagby . | |
| 4,743,256 | 5/1988 | Brantigan . | |
| 4,834,757 | 5/1989 | Brantigan . | |
| 4,877,020 | 10/1989 | Vich . | |
| 4,878,915 | 11/1989 | Brantigan . | |
| 4,936,851 | 6/1990 | Fox et al. . | |
| 4,961,740 | 10/1990 | Ray et al. . | |
| 4,978,350 | 12/1990 | Wagenknecht . | |
| 5,015,247 | 5/1991 | Michelson . | |
| 5,015,255 | 5/1991 | Kuslich . | |

(List continued on next page.)

FOREIGN PATENT DOCUMENTS

| | | |
|---|---|---|
| 0077159 | 4/1983 | European Pat. Off. . |
| 0716840 | 12/1995 | European Pat. Off. . |
| 0796593 | 9/1997 | European Pat. Off. . |
| 736213 | 11/1932 | France . |
| 2706309 | 6/1993 | France . |
| 2542056 | 3/1977 | Germany . |
| 8524537 | 1/1987 | Germany . |
| 4328690 | 8/1993 | Germany . |
| 9522946 | 8/1995 | WIPO . |
| 9532673 | 12/1995 | WIPO . |
| 9535180 | 12/1995 | WIPO . |
| 9627321 | 9/1996 | WIPO . |
| 9627339 | 9/1996 | WIPO . |

OTHER PUBLICATIONS

Posterior Lumbar Interbody Fusion Made Simple, Neurological Surgery Associates of Cincinnati, Inc.
Scientix Brochure, Cage CH, "Lumbar Spacing Cages".
Intervertebral Body Fusion By the Use of Posterior Bone Dowel, Benjamin R. Wilterberger, M.D., pp. 69–79.
A Technique of Posterior Cervical Fusion for Instability of the Cervical Spine, Davey et al. (1984).
Surgical Dynamics Brochure, Ray Ti for Interbody Fusion, Investigational Device, (1994).
Stryker Implants Brochure, Ogival Interbdoy Cage, Surgical Technique.
Unilateral Posterior Lumbar Interbody Fusion; Simplified Duel Technique, Blume (1984).

*Primary Examiner*—Michael Buiz
*Assistant Examiner*—Julian W. Woo

[57] ABSTRACT

A method for performing a surgical procedure includes the steps of providing a surgical retractor including a sleeve member having two opposed retractor arms at its distal end portion, at least partially inserting the retractor arms of the retractor within a space defined between adjacent bony structures whereby first and second supporting surfaces of each retractor arm respectively engage the opposed structures thereby distracting the structures, and performing the surgical procedure. A method for inserting a spinal implant is also disclosed. Instrumentation for performing the procedure is also disclosed.

26 Claims, 13 Drawing Sheets

U.S. PATENT DOCUMENTS

| | | |
|---|---|---|
| 5,026,373 | 6/1991 | Ray et al. . |
| 5,055,104 | 10/1991 | Ray . |
| 5,062,845 | 11/1991 | Kuslich et al. . |
| 5,263,953 | 11/1993 | Bagby . |
| 5,358,511 | 10/1994 | Gatturna et al. . |
| 5,400,805 | 3/1995 | Warren . |
| 5,431,658 | 7/1995 | Moskovich . |
| 5,454,811 | 10/1995 | Huebner . |
| 5,458,638 | 10/1995 | Kuslich et al. . |
| 5,470,334 | 11/1995 | Ross et al. . |
| 5,480,403 | 1/1996 | Lee . |
| 5,484,437 | 1/1996 | Michelson .................. 606/61 |
| 5,489,307 | 2/1996 | Kuslich et al. . |
| 5,489,308 | 2/1996 | Kuslich et al. ............ 623/17 |
| 5,505,732 | 4/1996 | Michelson . |
| 5,522,899 | 6/1996 | Michelson . |
| 5,534,031 | 7/1996 | Matsuzaki et al. . |
| 5,549,679 | 8/1996 | Kuslich . |
| 5,554,191 | 9/1996 | Lahille et al. . |
| 5,562,736 | 10/1996 | Ray et al. . |
| 5,571,109 | 11/1996 | Bertagnoli . |
| 5,571,189 | 11/1996 | Kuslich . |
| 5,571,192 | 11/1996 | Schönhöffer . |
| 5,591,235 | 1/1997 | Kuslich . |
| 5,593,409 | 1/1997 | Michelson . |
| 5,609,635 | 3/1997 | Michelson . |
| 5,609,636 | 3/1997 | Kohrs et al. . |
| 5,741,253 | 4/1998 | Michelson . |
| 5,797,909 | 8/1998 | Michelson . |

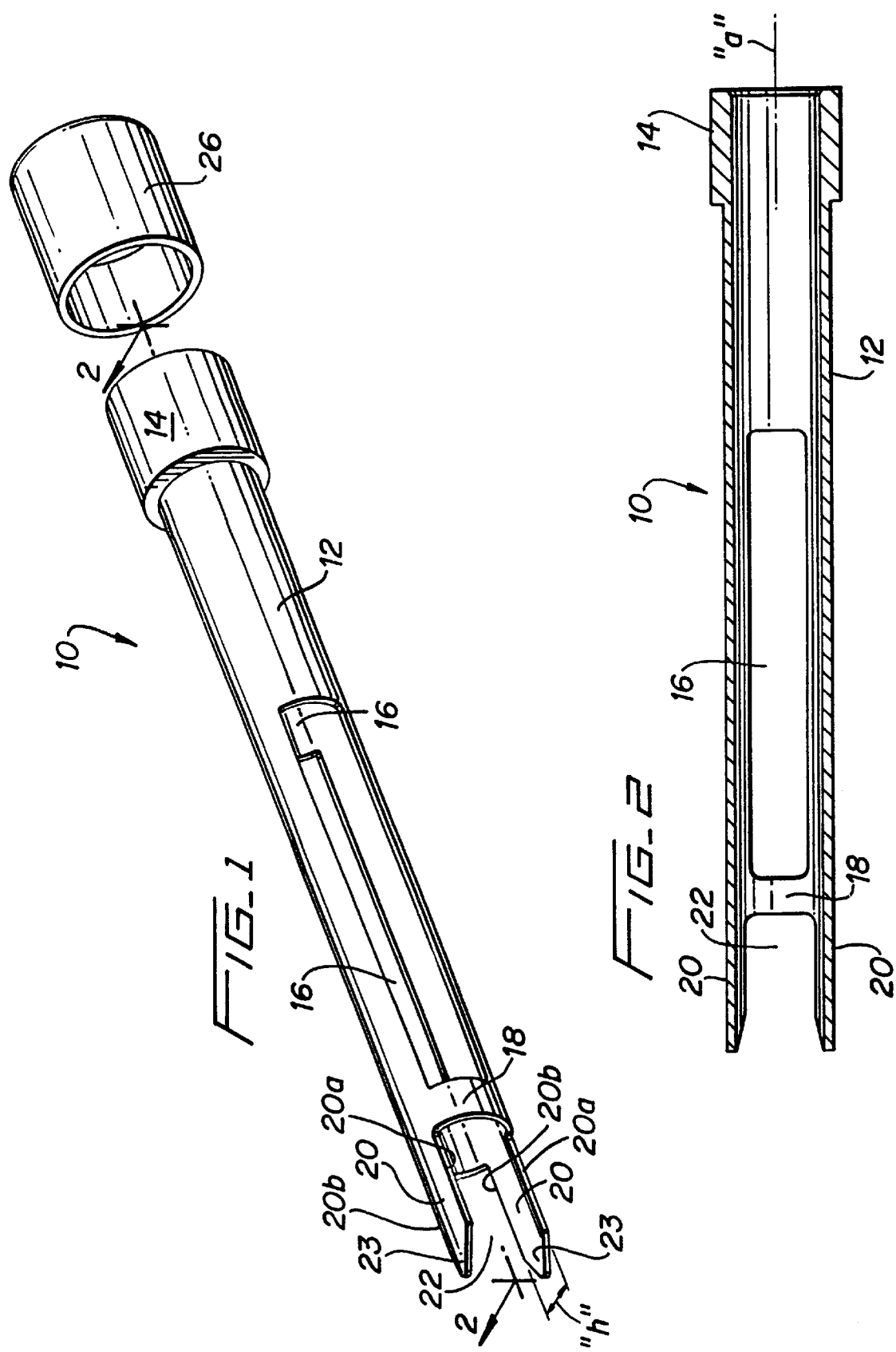

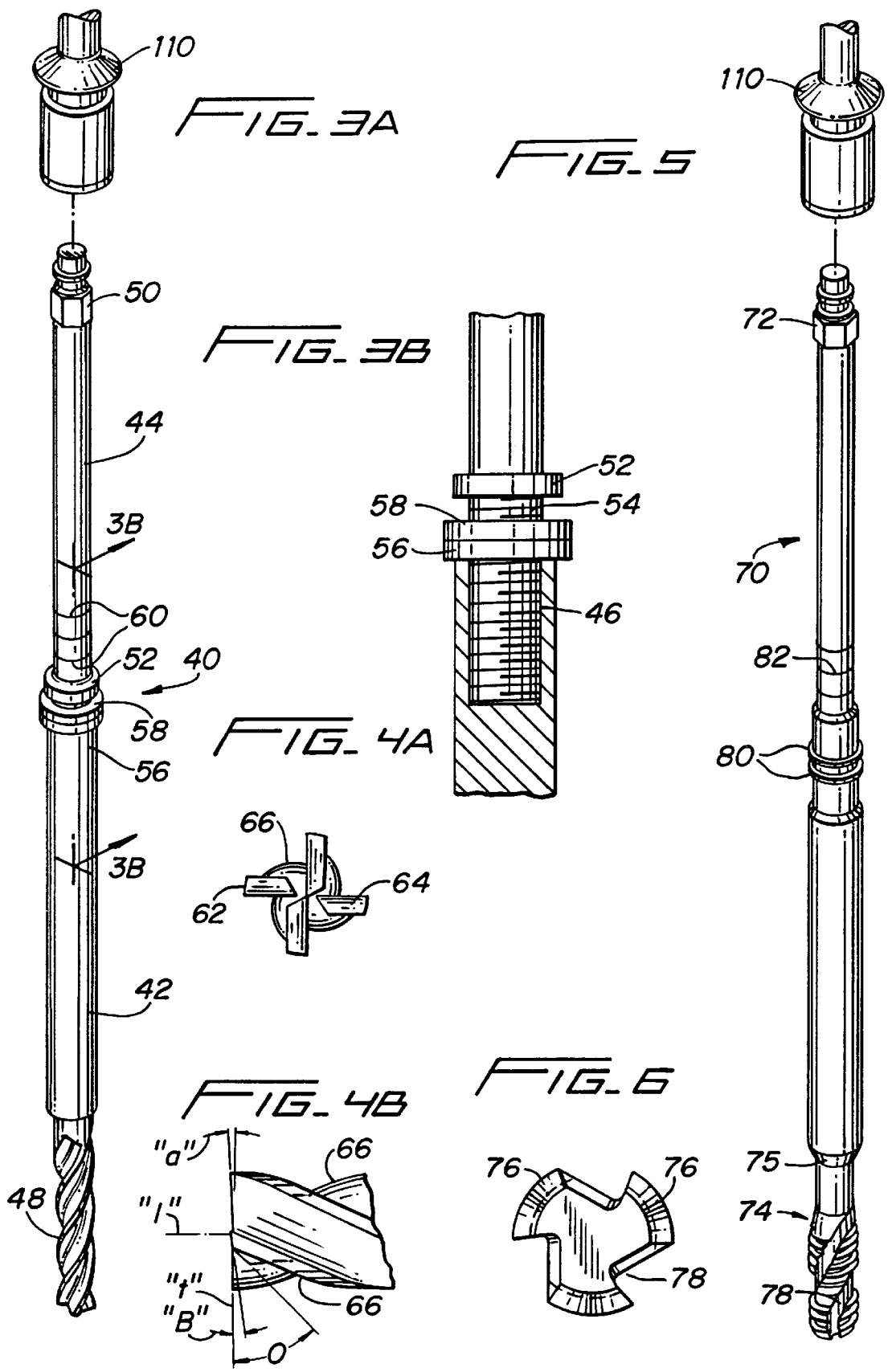

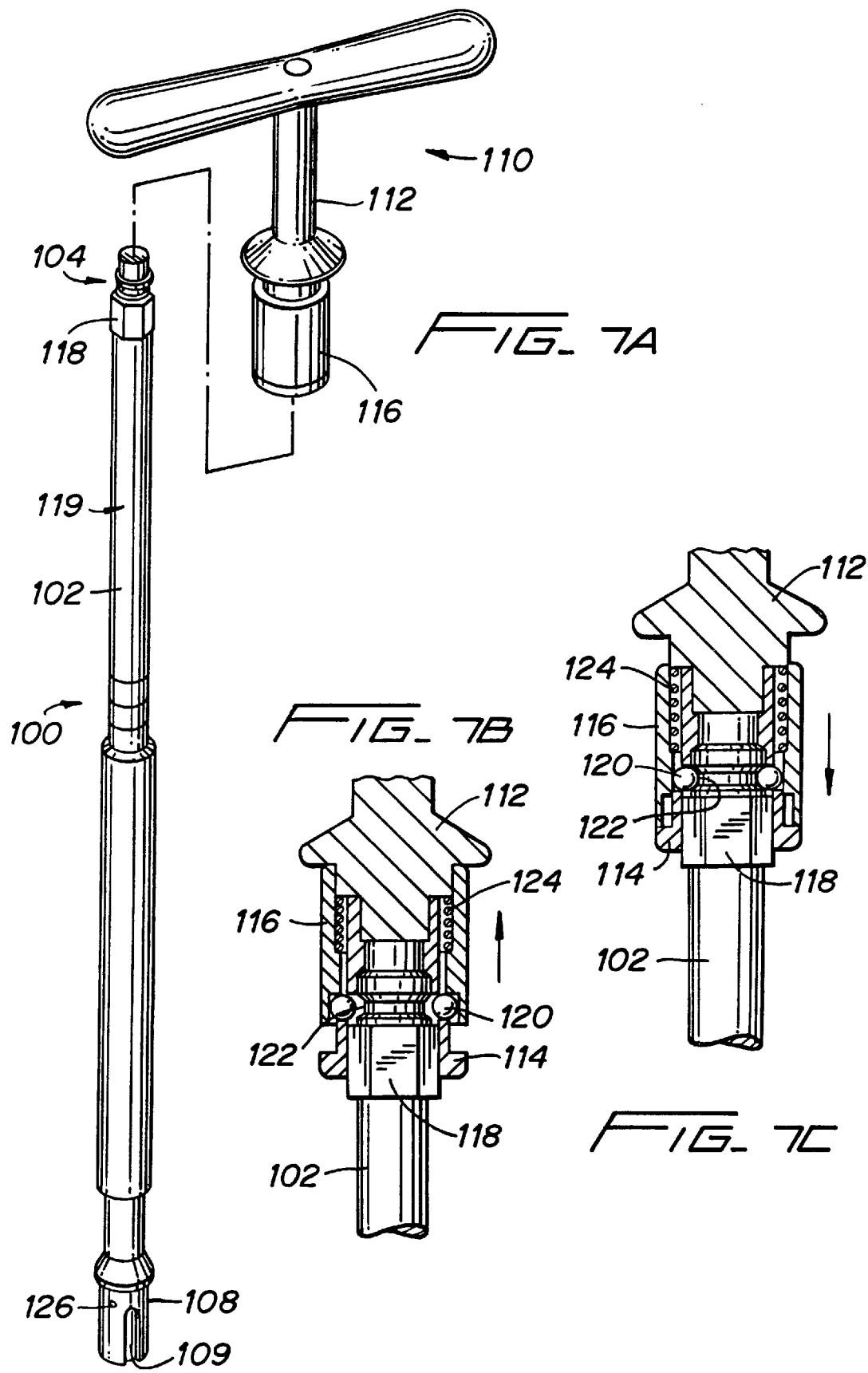

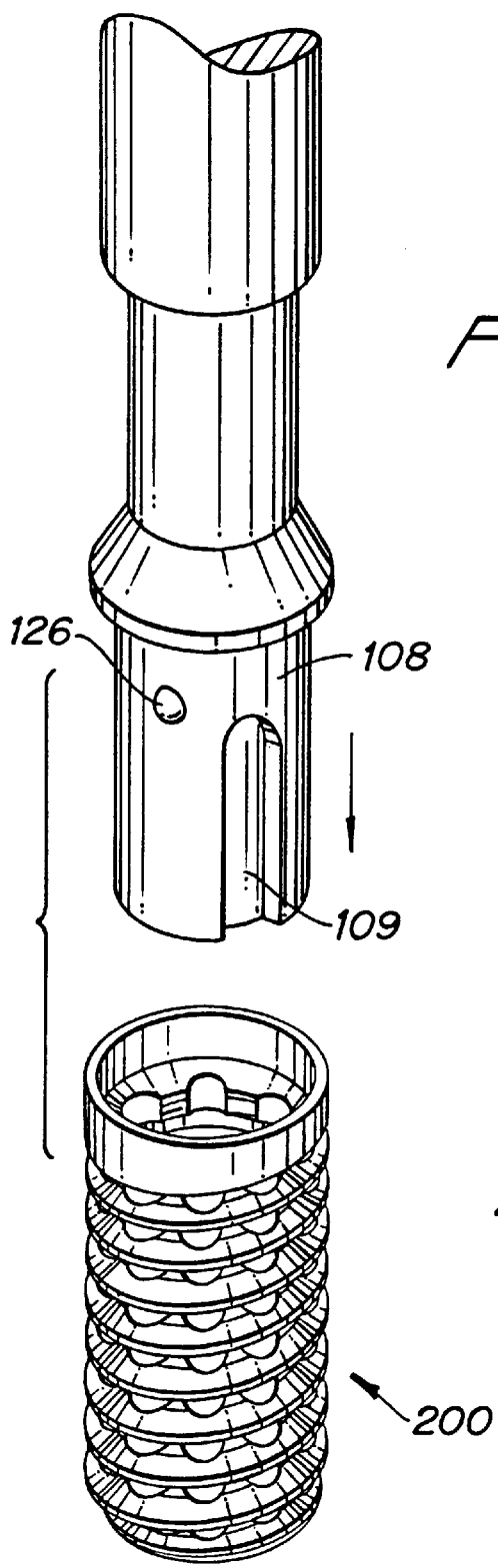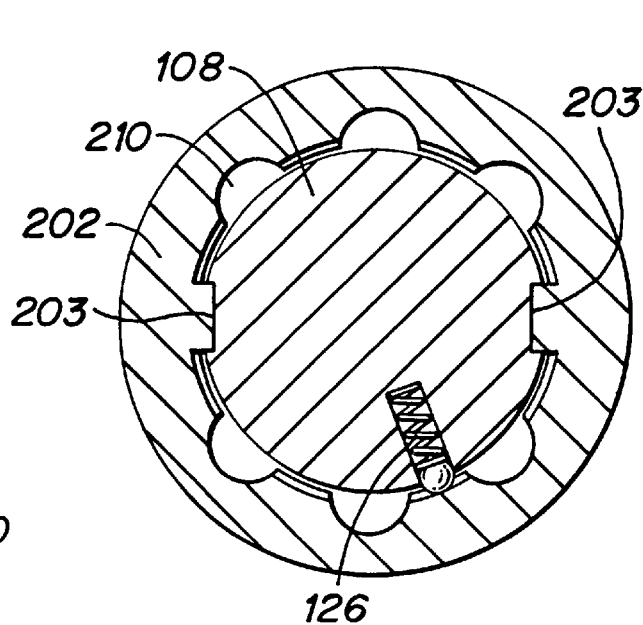
FIG. 10A
FIG. 10B

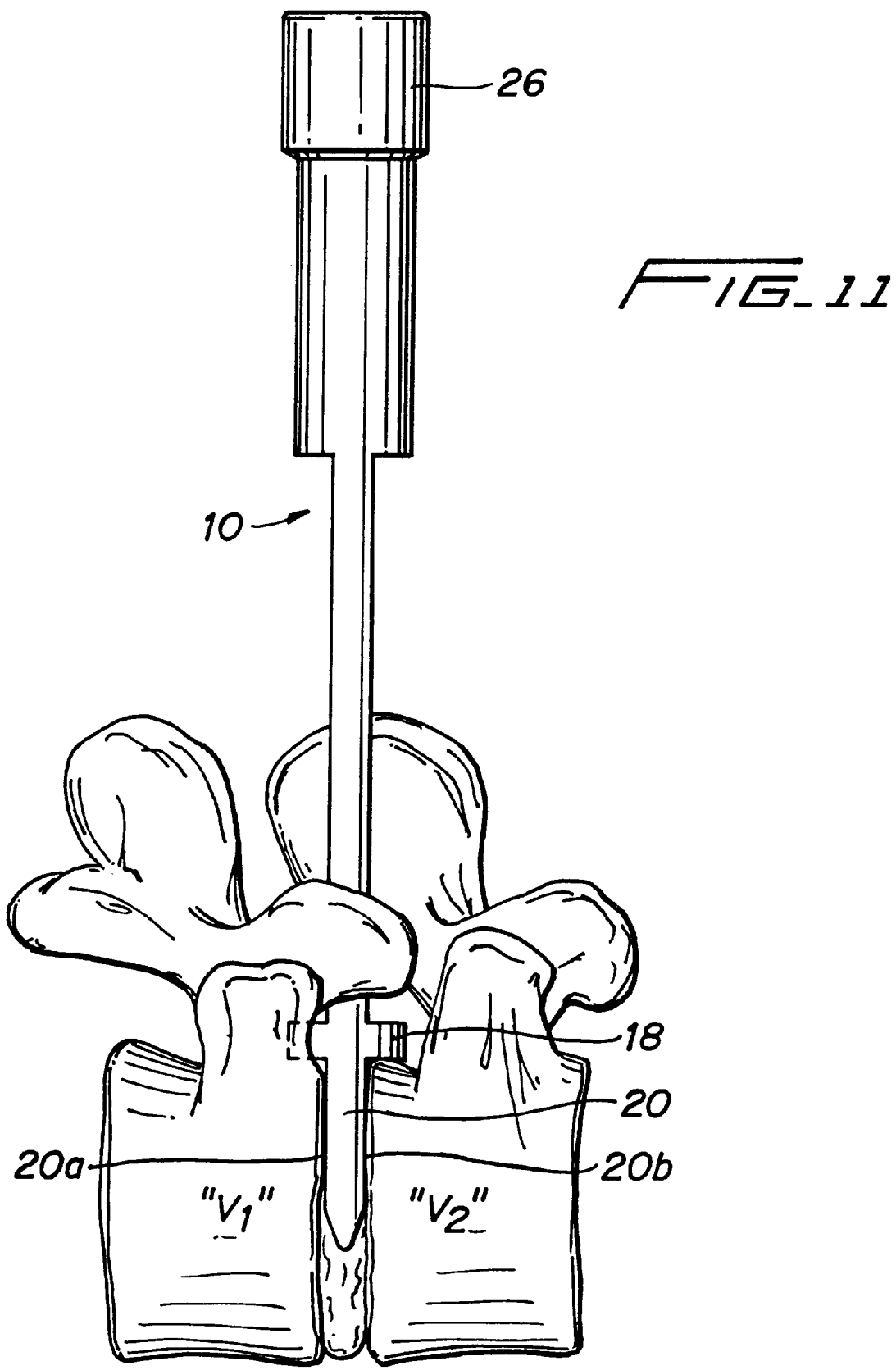
FIG_11

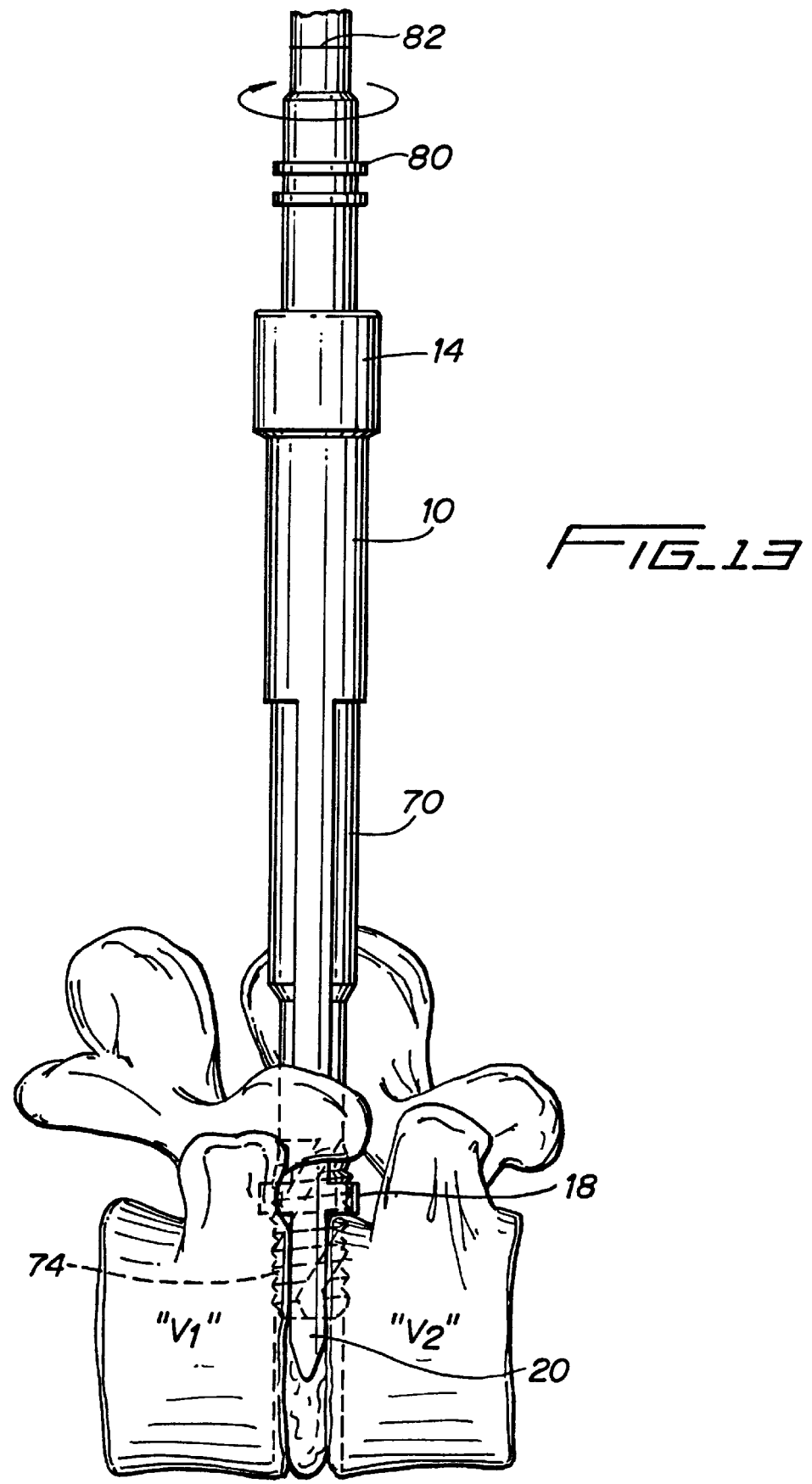

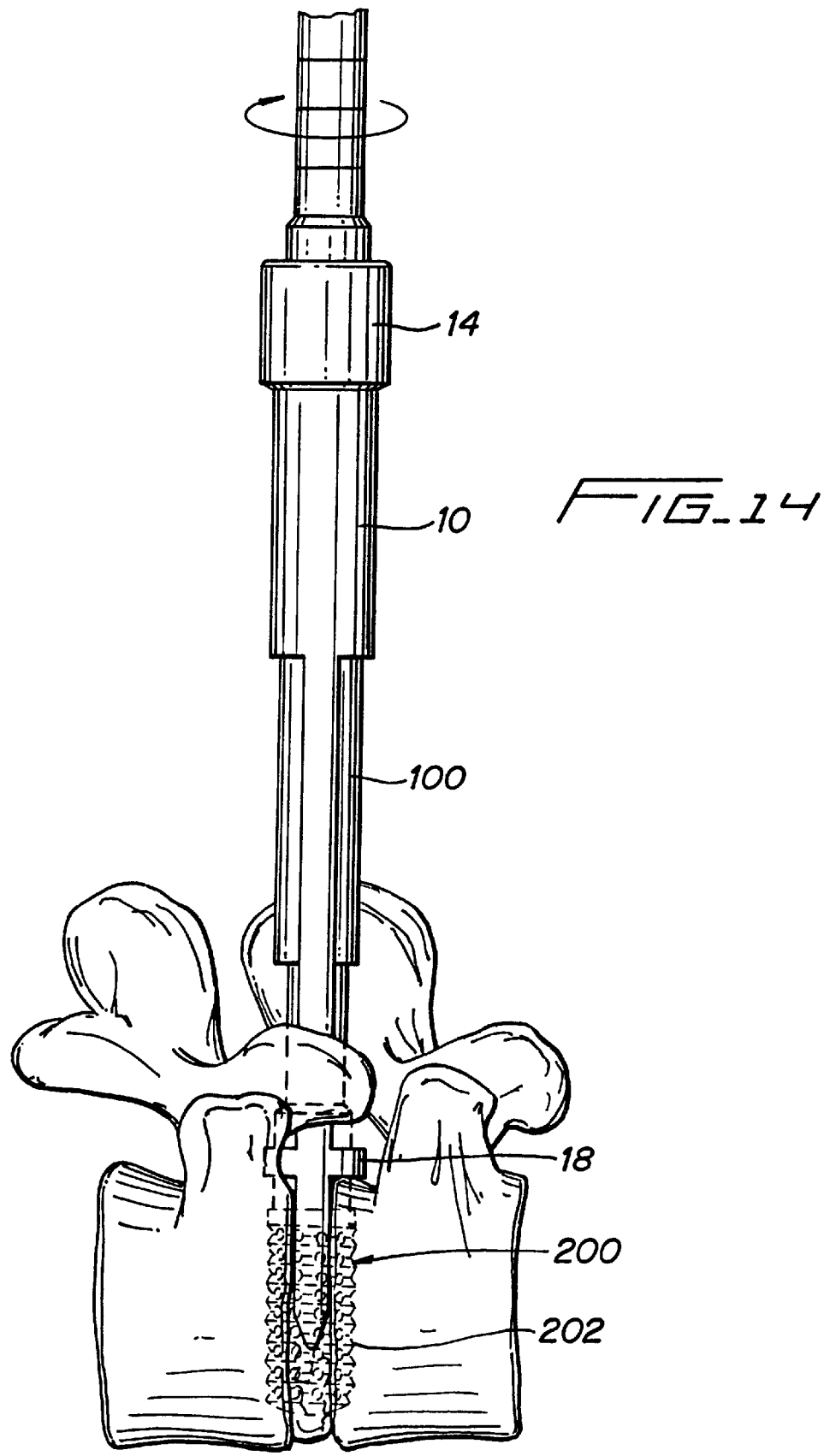
FIG_14

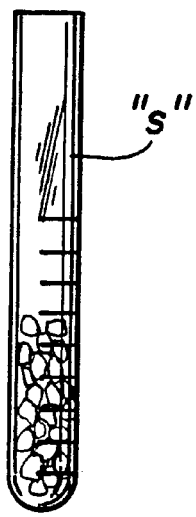
FIG_15
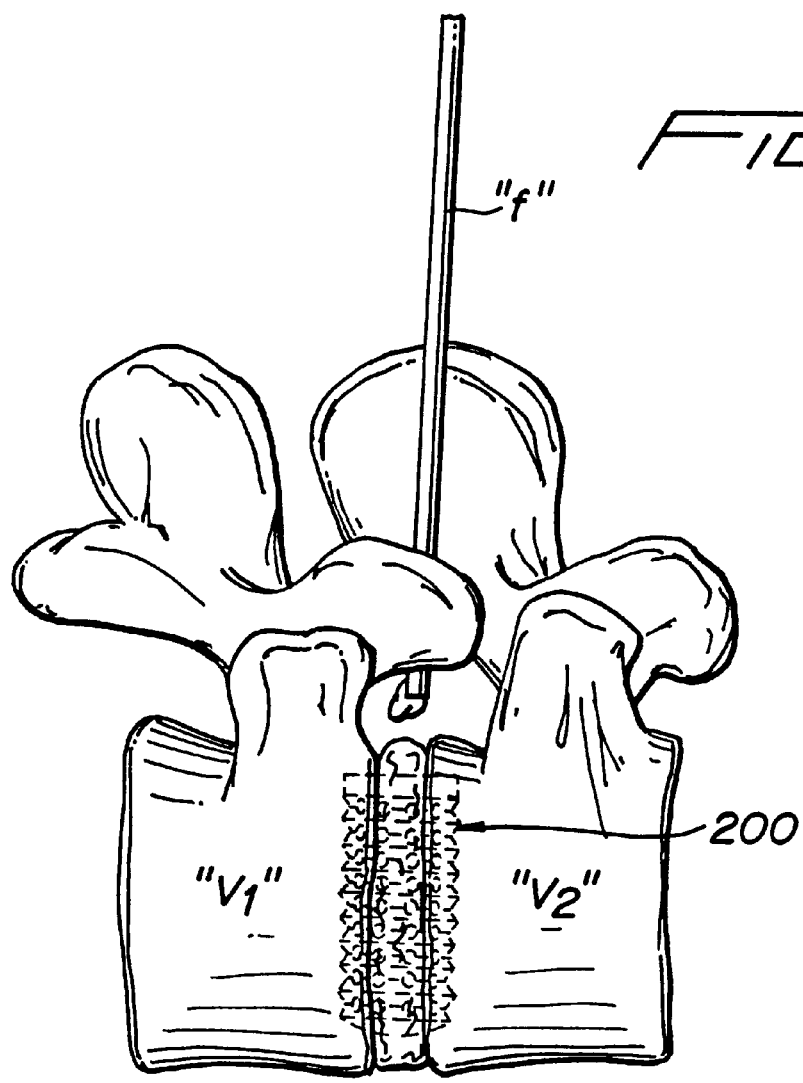
FIG_16

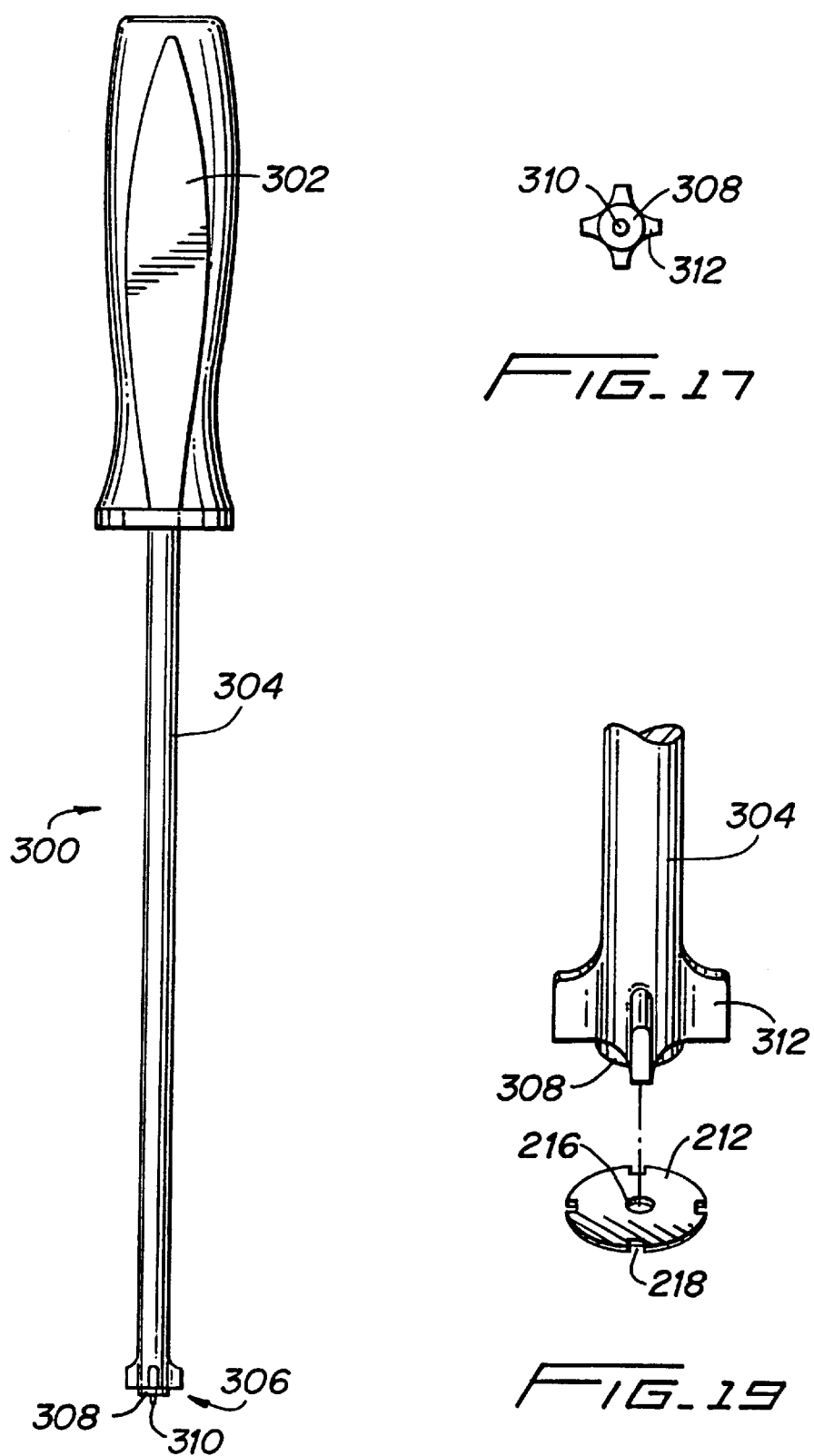

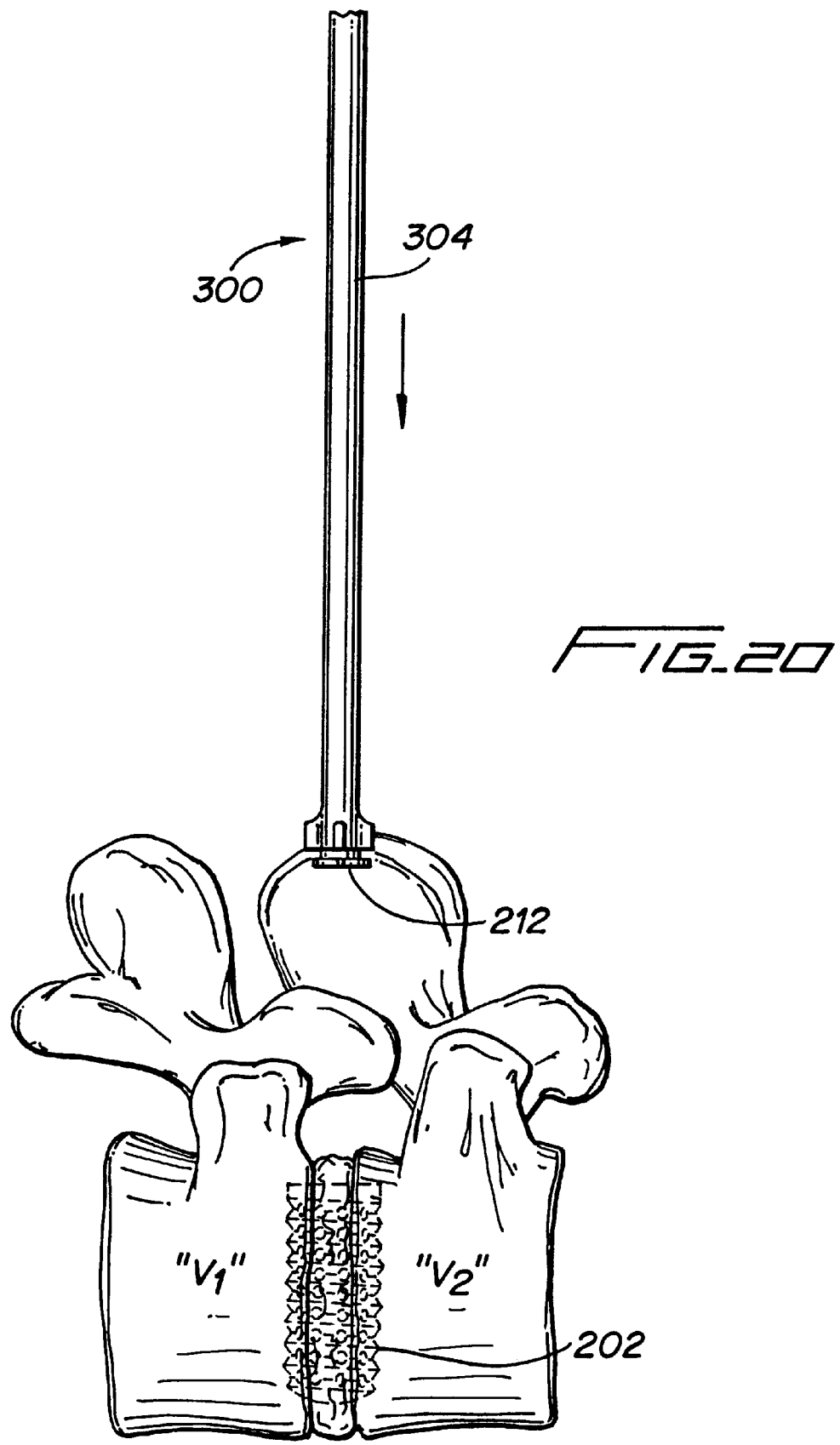

METHOD AND INSTRUMENTATION FOR IMPLANT INSERTION

This is a continuation of U.S. application Ser. No. 08/615,379, filed Mar. 14, 1996 now abandoned.

BACKGROUND

1. Technical Field

The present disclosure generally relates to a method and associated instrumentation for implant insertion and, in particular, to a method and instrumentation for insertion of spinal implants to facilitate fusion of adjacent vertebral bodies.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. No. 5,470,334 to Ross et al.; U.S. Pat. No. 5,454,811 to Huebner; U.S. Pat. No. 5,480,403 to Lee et al.; U.S. Pat. No. 5,400,805 to Warren; U.S. Pat. No. 5,358,511 to Gattuma et al.; and U.S. Pat. No. 4,877,020 to Vich.

Some implants are particularly configured with cavities and bores to facilitate bony in growth and enhance anchoring of the implant at the insertion site. See, for example, U.S. Pat. No. 4,328,593 to Sutter et al.; U.S. Pat. No. 4,936,851 to Fox et al.; and U.S. Pat. No. 4,878,915 to Brantigan. Implants in the form of fusion cages having internal cavities to receive bone growth stimulation materials such as bone chips and fragments are disclosed, for example, in U.S. Pat. No. 4,501,269 to Bagby; U.S. Pat. No. 4,961,740 to Ray et al.; U.S. Pat. No. 5,015,247 to Michaelson; and U.S. Pat. No. 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, the contents of which are incorporated herein by reference.

Both anterior (transabdorninal) and posterior surgical approaches are used for interbody fusions of the lumbar spine. Fusions in the cervical area of the spine are primarily performed using a posterior approach. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized canceilous region to facilitate bone growth across the implant.

One of the more critical tasks performed in the insertion of a surgical fusion implant, particularly, in intervertebral spinal fusion, is the formation of the implant receiving cavity or bore between/within the adjacent vertebrae. More particularly, the drilled bore must be equally centered within the intervertebral space and preferably parallel to the vertebral end plates to ensure removal of equal portions of bone from the adjacent vertebrae throughout the length of the cut and subsequent appropriate seating of the implant relative to the vertebral bodies.

Surgical instruments for spinal fusion implant insertion are known. For example, U.S. Pat. No. 5,484,437 to Michelson discloses a method and apparatus incorporating an outer and an inner sleeve arrangement. The outer sleeve is positioned over the spinal distractor and has teeth at one end which are driven directly into the posterior surface of the adjacent vertebrae. The inner sleeve is positioned within the outer sleeve and serves to guide instruments such as a drill used to form the implant receiving bore. U.S. Pat. No. 5,487,307 to Kuslich et al.; U.S. Pat. No. 5,015,247 to Michelson; and U.S. Pat. No. 4,878,915 to Brantigan also disclose outer sleeves with teeth mounted to the vertebrae. Other arrangements include the use of guide rods which are placed in pilot holes formed in the vertebral bodies. The guide rods guide a bore forming hollow drill into the intervertebral space.

Although some current instrumentation and methods associated therewith for enhancing the placement of spinal fusion implants have been generally effective for their intended purposes, there exists certain limitations with the design of this instrumentation which detract from their usefulness. For example, the arrangement disclosed in the Michelson '437 patent and similar arrangements do not provide for automatic alignment of the outer sleeve to ensure that the bore formed by a drill introduced into the outer sleeve is in optimal alignment for a tapping procedure (if required) and reception of the spinal implant. Rather, such orientation is dependent directly upon the skill of the surgeon. Moreover, the outer sleeve, which is mounted via teeth only at its extreme distal end to the posterior surface of the adjacent vertebrae, is subject to disorientation or dislodgment during insertion and/or removal of the drill and/or tapping instrument. The use of guide rods increases the number of steps required to implant the fusion cage.

Accordingly, the present disclosure is directed to a method and associated instrumentation to facilitate the introduction of a fusion implant, which ensures optimal alignment of the drilled bore for reception of the fusion implant and, if appropriate, for bore tapping procedures. The instrumentation of the present disclosure also reduces the number of steps required for implantation of the fusion cage.

SUMMARY

Generally, the present disclosure is related to a method for performing a surgical procedure. The method includes the steps of providing a surgical retractor having proximal and distal end portions and having an opening therethrough to receive instrumentation, the distal end portion configured for insertion at least partially into an intervertebral space between adjacent opposed vertebrae. The method further includes the steps of at least partially inserting the retractor into the intervertebral space to distract adjacent vertebral and performing the surgical procedure with instrumentation inserted through the retractor. The surgical procedure particularly contemplated includes introducing a fusion implant through the surgical retractor and within the space defined between the distracted vertebrae.

The present disclosure is also directed to a method for effecting fusion of adjacent vertebral bodies, including the steps of accessing the intervertebral disc space, providing a retractor including a retractor sleeve having proximal and distal end portions with the distal end portion having opposed retractor arms extending in a general longitudinal direction, positioning the retractor arms within the intervertebral disc space whereby first and second supporting surfaces of each arm contact and distract opposed vertebral bodies, introducing a drill instrument into the sleeve and advancing the drill instrument within the sleeve to the intervertebral disc space, forming with the drill instrument a bore that penetrates at least partially into each opposed vertebral body, removing the drill instrument from the sleeve and introducing a fusion implant into the bore. The preferred method may further include the steps of introducing a tap instrument into the sleeve and advancing the tap instrument within the sleeve to the disc space, tapping with the tap instrument a thread within the bore such that the thread communicates into the opposing vertebral bodies, removing the tap from the retractor sleeve, introducing a fusion implant having a cage body with an external thread into the bore and screwing the cage body into the threaded bore.

The preferred fusion implant has a plurality of openings extending through the cage body whereby bone-growth inducing substances may be introduced into the cage body of the fusion implant to fuse with the adjacent vertebral bodies.

The present disclosure is also directed to instrumentation utilized to perform the spinal fusion implant surgery. In particular, a surgical retractor is provided including an elongated member having proximal and distal end portions and defining a longitudinal passageway for reception of surgical instrumentation. The distal end portion of the member includes first and second retractor arms extending in a general longitudinal direction. Each retractor arm has first and second supporting surfaces for engaging opposed adjacent tissue portions, e.g. opposed vertebral bodies. Each retractor arm defines a dimension between the first and second supporting surfaces sufficient to distract the opposed tissue portions, e.g. vertebral bodies, upon insertion thereof. The retractor arms may each possess distal tapered portions for facilitating insertion into the intervertebral space. The first and second supporting surfaces of each retractor arm are preferably in general parallel relation to each other and the longitudinal axis of the sleeve member and in a preferred embodiment are substantially planar.

The present disclosure is also directed to a surgical tapping instrument for tapping an internal thread within a bore defined in adjacent vertebral bodies. The tapping instrument includes an elongated frame defining a longitudinal axis and having a distal tapping head. The tapping head includes a tapping thread for tapping a thread within the bony tissue and at least one conveyance channel having a directional component transverse to the longitudinal axis and dimensioned to collect bone material removed during the tapping procedure.

Other instrumentation to facilitate spinal implant insertion is also disclosed.

BRIEF DESCRIPTION OF THE DRAWINGS

Preferred embodiments of the disclosure are described hereinbelow with reference to the drawings wherein:

FIG. 1 illustrates a surgical retractor constructed in accordance with the principles of the present disclosure and utilized in distracting adjacent bony structures;

FIG. 2 is a cross-sectional view of the retractor taken along the lines 2—2 of FIG. 1;

FIG. 3A is a perspective view of a drilling instrument utilized in drilling a bore within the adjacent bony structures;

FIG. 3B is a cross-sectional view of the drilling instrument taken along the lines 3B—3B of FIG. 3A;

FIG. 4A is an axial plan view of the drilling head of the drilling instrument;

FIG. 4B is a side plan view of the distal end portion of the drilling head illustrating the end and side cutting surfaces of the drilling head;

FIG. 5 is a perspective view of a tapping instrument utilized in tapping an internal thread in the bore formed by the drilling instrument;

FIG. 6 is an axial plan view of the tapping head of the tapping instrument of FIG. 5;

FIG. 7A is a perspective view of an insertion instrument and a detached T-handle utilized in inserting an implant within the tapped bore formed by the tapping instrument;

FIG. 7B is an enlarged cross-sectional view illustrating a mounting arrangement for mounting the T-handle to the insertion instrument with the mounting mechanism in a disengaged position;

FIG. 7C is a view similar to the view of FIG. 7B illustrating the mounting mechanism in an engaged position;

FIG. 10A is a perspective view illustrating mounting the distal end of insertion instrument of FIG. 7A to the implant of FIG. 8;

FIG. 10B is a cross-sectional view illustrating engagement of the spring-loaded ball detent of the insertion instrument with the interior surface of the implant;

FIG. 11 is a side plan view illustrating positioning of the retractor of FIG. 1 within an intervertebral space between adjacent vertebrae in accordance with a preferred method for inserting the implant;

FIG. 13 is a side plan view illustrating insertion of the tapping instrument of FIG. 5 into the retractor to tap an internal thread in the bore;

FIG. 14 is a side plan view illustrating insertion of the insertion instrument with mounted implant through the retractor and placement of the implant within the tapped bore;

FIG. 15 is a side plan view of a syringe containing bone inducing substances;

FIG. 16 is a side plan view illustrating loading of the bone-inducing substances into the implant with the use of forceps;

FIG. 17 is a side plan view of a cap mounting instrument utilized in mounting the implant end cap onto the body of the implant;

FIG. 18 is an axial plan view of the mounting head of the mounting instrument of FIG. 17;

FIG. 19 is a perspective view of the mounting head and the end cap;

FIG. 20 is a view illustrating insertion of the mounting instrument and end cap within the surgical site to mount the end cap to the body of the implant.

DETAILED DESCRIPTION OF THE PREFERRED EMBODIMENT(S)

Figure 8:
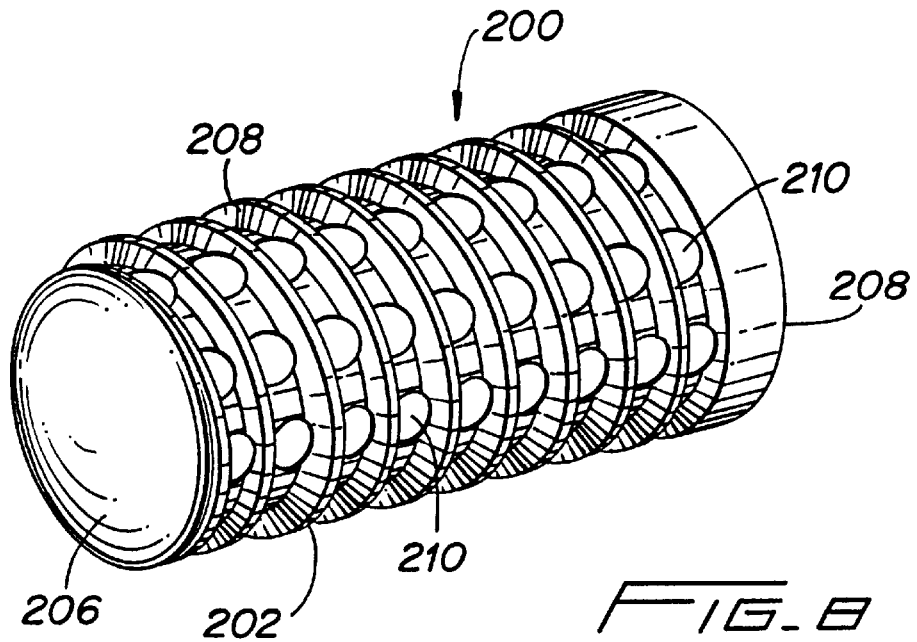
FIG. 8 is a perspective view of the implant to be inserted into the tapped bore formed between the adjacent bony structures.

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of each instrument utilized in performing a spinal fusion followed by a description of the preferred method for spinal fusion utilizing the instrumentation in accordance with the present disclosure.

In the discussion which follows, the term "proximal", as is traditional, will refer to the portion of the structure which is closer to the operator, while the term "distal" will refer to the portion which is further from the operator.

Referring now to the drawings in which like reference numerals identify similar or identical elements throughout the several views, FIG. 1 illustrates in perspective view a surgical retractor of the present disclosure. Retractor 10 is particularly contemplated for distracting adjacent bony structures, e.g., adjacent opposed vertebral bodies, to facilitate the insertion and application of an implant, for providing a cannula for insertion of the instruments, and for ensuring proper alignment of the instrumentation and accurate insertion of the implant. Although described for spinal procedures, it is envisioned that retractor 10 may also be utilized to distract other structures as well including joints, ligaments, etc.

Referring now to FIGS. 1–2, retractor 10 includes sleeve 12 defining longitudinal axis "a" and having enlarged head 14 disposed at a proximal end thereof. Sleeve 12 defines a longitudinal opening extending therethrough to receive surgical instrumentation described below. Sleeve 12 and enlarged head 14 are preferably monolithically formed of a suitable rigid material including stainless steel, aluminum alloy or the like. Sleeve 12 may be formed of a suitable polymeric material as well. Sleeve 12 may be a variety of sizes including, for example, 12 mm, 14 mm, 16 mm and 18 mm in diameter. The retractor size utilized will generally correspond to the diameter of the instrumentation and/or implant to be applied.

Sleeve 12 may include first and second longitudinally extending openings 16 formed in its outer wall. Openings 16 are diametrically arranged with relation to each other and terminate at their distal ends in collar 18. Each opening 16 extends radially for about between 10%–50% the circumference or perimeter of sleeve 12 and longitudinally for greater than 50% the length of sleeve 12. Openings 16 are contemplated to permit the lateral introduction of surgical instrumentation required to carry out the fusion procedure as an alternative to introducing the instrumentation through the open proximal end of sleeve 12. These openings 16 also enhance illumination at the surgical site.

Sleeve 12 further includes first and second diametrically opposed retractor arms or tangs 20. Retractor arms 20 extend distally from collar 18 in a general longitudinal direction parallel to one another and define longitudinal slotted portion 22. Each arm 20 has an arcuate outer surface (i.e., defining a radius of curvature substantially equivalent to the radius of curvature of the remaining portion of the sleeve). Each retractor arm 20 has first and second vertebrae supporting surfaces 20a, 20b in general parallel relation to each other and preferably parallel to the longitudinal axis of sleeve 12. In the illustrated embodiment, supporting surfaces 20a, 20b are substantially planar. The height "h" of each arm 20 (i.e., the distance between supporting surfaces 20a, 20b) corresponds to the height of the intended distraction distance between adjacent tissue portions, i.e. adjacent vertebrae. For example, in spinal fusion application, the height "h" of each arm 20 ranges from about 0.3 to 0.4 inches and more preferably from about 0.28 to about 0.35 inches. One skilled in the art will readily appreciate that this dimension can be varied as needed depending upon the procedure. Each arm 20 further includes tapered end portions 23 defining a generally V-shaped configuration. End portions 24 facilitate insertion of retractor arms 20 within the surgical site, e.g., within the intervertebral space.

Referring still to FIGS. 1–2, an impact end cap 26 is positionable over enlarged head 14 and preferably has an inner diameter approximating the outer diameter of the head 14 to form a releasable frictional fit between the two components. Impact cap 26 is intended to receive the impact of a driving instrument used to insert retractor 10 within the bony tissue as will be discussed. Such impaction, drives the arms 20 of sleeve 12 into the disc space (with the height h spanning the space) and distracts the opposing vertebrae bodies as surfaces 20a engage the upper (or lower) vertebral body and surface 20b engages the opposing vertebral body, thereby firmly mounting the retractor 20 to maintain its alignment and orientation and ensure that an equal amount of material is cut on both vertebral end plates when a drill is inserted therethrough (described below).

Referring now to FIGS. 3A–3B, the drilling instrument used to form a bore between/within the adjacent vertebrae will be described. Drilling instrument 40 includes drill shaft 42 and extension shaft 44 which is connectable to the drill shaft 42. Drill shaft 42 has an internally threaded bore 46 at its proximal end and drill bit 48 mounted at its distal end. Extension shaft 44 has a proximal mounting section 50 which cooperatively engages corresponding structure of a T-handle (the distal portion of the T-handle is depicted in FIG. 3A) to mount the handle to the extension shaft 44. The particular mounting arrangement utilized to effect the mounting of the T-handle to extension shaft 44 will be discussed in greater detail hereinbelow with later reference to FIGS. 7A–7C. Extension shaft 44 further includes collar 52 and distal threaded portion 54 extending from the collar 52. Collar 52 includes an internal thread which cooperates with threaded portion 54 to mount the collar 52 to extension shaft 44. Collar 52 is preferably fixedly mounted to threaded portion 54 by welding or the like. Distal threaded portion 52 cooperatively engages internal threaded bore 46 of drill shaft 42 to connect the two components.

Extension shaft 44 has first and second collars 56, 58 which are threaded on threaded portion 54. Each collar 56, 58 is moveable on threaded portion 54 between a position adjacent stationery collar 52 and a position adjacent drill shaft 42. First collar 56 serves as a positioning collar, i.e., by adjusting the positioning of first collar 56 on threaded portion 54, the depth of penetration of drill shaft 42 into the bony structures may be adjusted. Second collar 58 serves as a locking collar to selectively lock the first collar 56 at the predetermined location on threaded portion 54. In particular, when drilling instrument 40 is inserted within sleeve 12 of the retractor of FIG. 1, positioning collar 56 engages the proximal end face of enlarged head 14, thus, precluding further distal advancement of drilling instrument 40 within the bony structures. Thus, by selectively adjusting the location of positioning collar 56 on threaded portion 54 and locking the collar 56 with locking collar 58 at the desired position, the length (depth) of the bore formed in the bony structures (e.g., vertebrae) is readily controllable. Thus, the depth of the hole is predetermined to accommodate the length of the fusion cage to be implanted. Extension shaft 44 also includes depth markings 60 on its outer surface. Depth markings 60 are calibrated to indicate to the surgeon the degree of penetration of drill shaft 42, thus, further assisting the surgeon in monitoring the length of the bore formed by drilling instrument 40.

Referring now to FIGS. 4A–4B, drill bit 48 includes a twin cutting surface design incorporating end cutting edges 62 located on flutes 64 and side cutting edges 66. These edges 62, 66 cooperate to shear or cut the tissue rather than tear or pull the soft tissue as in conventional bone drills. The end cutting edge 62 cleanly cuts the soft disc material as the side cutting edges 66 cut the end plates substantially simultaneously. Thus, the bore formed by drill bit 48 is clean and exceptionally precise and less manual pressure on the drill is required to form the hole. As depicted in FIG. 4B, which is an enlarged view of the distal end portion of drill bit 48, the drill bit 48 defines the following parameters. Angle "a" is the degree of forward projection of the outer peripheral surface of the distal end of the drill bit 48 relative to a plane "t" transverse to the longitudinal axis "l" defined by the radial center of the drill bit 48. Angle "a" ranges from about 0° to about 10° and is preferably about 2°. Angle "B" is the degree of the angle of attack for end cutting edges 62 relative to the transverse plane "t" and ranges from about 2° to about 15°, and is preferably about 5°. Angle "O" is the degree of twist defined by side cutting edges 62 relative to the transverse plane "t" and ranges from about 15° about 60°, and is preferably about 45°.

Referring now to FIGS. 5–6, tapping instrument for forming an internal thread within the drilled bore will be discussed. Tapping instrument 70 includes proximal mounting portion 72 which cooperatively engages T handle (discussed below) and distal tapping thread portion 74. Distal tapping thread portion 74 includes threaded cutting edges 76 and at least one spiral conveyance channel [3 are shown] extending longitudinally from the distal end of tapping thread portion 74 to the proximal end of the thread portion 74. The conveyance channels having a directional component transverse to the longitudinal axis and preferably in the form of a helical groove. Conveyance channel 78 is dimensioned to receive bone material deburred by the cutting edges 76 during the tapping procedure and to continually transmit the bone material proximally through the channel 78 to avoid undesired material build-up at the tapping site. In this manner, tapping instrument 70 may be used to completely tap the internal thread within the bore without interruption of the tapping procedure.

Tapping instrument 70 further includes annular rings 80 integrally formed at an intermediate portion of the instrument. Annular rings 80 facilitate grasping engagement of tapping instrument 70 by the user. Several depth markings 82 are provided on the external surface of the tapping instrument 70. Depth markings 82 indicate the depth of insertion of tapping instrument 70 within the retractor 10 of FIG. 1 and the bore defined in the adjacent bony structures. Bevel 75 facilitates insertion of the tapping instrument 70 into the retractor 10.

Referring now to FIGS. 7A–7C, the insertion instrument for inserting the fusion implant into the tapped bore and the T-handle will be discussed. Insertion instrument 100 includes elongated member 102 having handle mounting section 104 at its proximal end and rounded head 108 at its distal end. Although the elongated member 102 is shown having sections of different diameters, in an alternate embodiment, the elongated member 102 is of substantially uniform diameter between its proximal and distal end portions. Handle mounting section 104 is configured to engage T-handle 110 to mount the T-handle to the insertion instrument. In a preferred mounting arrangement, T-handle 110 includes handle body 112, a first sleeve 114 mounted to the body 112 and a second sleeve 116 mounted with respect to the first sleeve 114. First sleeve 114 has an inner surface correspondingly dimensioned to engage hexagonal portion 118 of handle mounting section 104. An internal spring loaded ball system 120 is defined adjacent second sleeve 116 and is configured to engage an annular groove 122 defined in handle mounting section 104. Second sleeve 116 is mounted for relative movement between an unlocked position (FIG. 7B) and a locked position (FIG. 7C). In the locked position, ball system 120 is forced radially inwardly into annular groove 122. Spring 124 normally biases second sleeve 116 to the locked position. As depicted in FIG. 7B, in the unlocked position, second sleeve 116 is retracted to release ball system from annular groove 122.

Handle mounting section 104 of insertion instrument 100 is identical to the mounting sections 50, 72 of drilling instrument 40 and tapping instrument 40, 70, respectively. Thus, T-handle 110 may be mounted and used with drilling instrument 40 and tapping instrument 70 in an identical manner.

Figure 9:
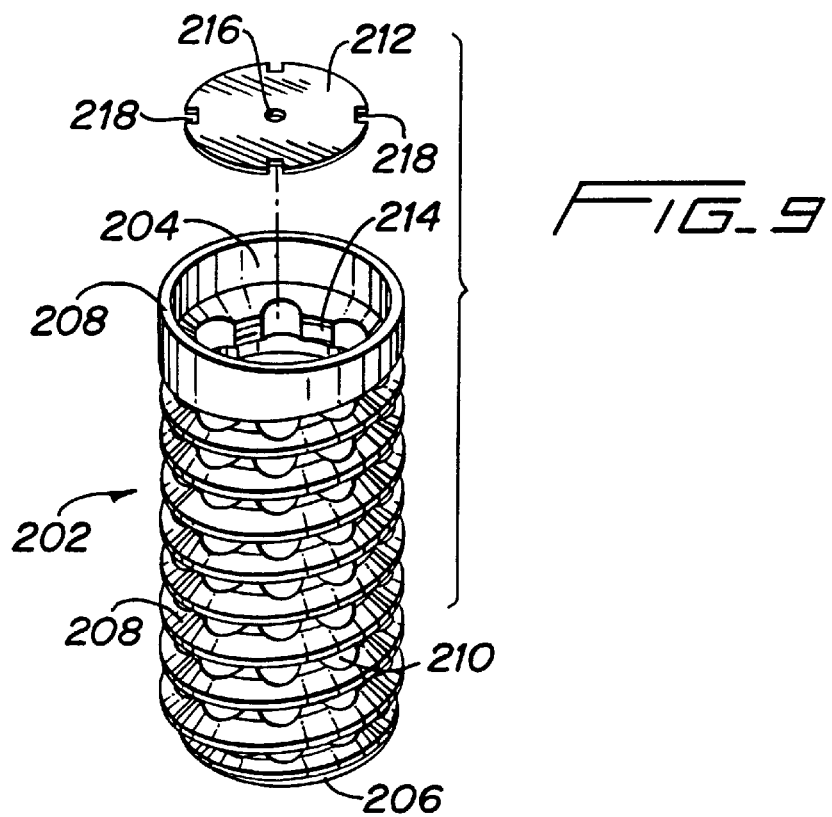
FIG. 9 is a perspective view of the implant of FIG. 8 illustrating the body and detached end cap.

Referring now to FIGS. 8–9, one type of implant designed for use in spinal fusion procedures and with which the instrumentation of the present disclosure can be used is illustrated. This implant is generally disclosed in U.S. Pat. No. 5,026,373 to Ray, the contents of which are incorporated herein by reference, and is commonly referred to as a "fusion cage".

Implant or fusion cage 200 includes body portion 202 having an internal cavity or hole 204 for accommodating bone-growth inducing substances. One end 206 of cage body 202 is closed and defines a rounded or bull-nosed configuration to facilitate insertion of the fusion cage relative to one or more bony structures. The other end 208 defines an opening which communicates with internal cavity 204. The outer surface of the cage body 202 includes a single continuous thread 208 (preferably V-shaped) having a plurality of raised turns with valleys defined between adjacent turns.

A plurality of perforations 210 are disposed within the threads and extend through the outer surface of the cage body 202 to provide direct communication between the outer surface and the inner cavity 204. The perforations 210 permit immediate contact between the bone growth inducing substances within the inner cavity 204 and the bone structure when the cage body 202 is mated to the bone structure, e.g., adjacent vertebrae. An end cap 212 is mountable to the open end of cage body 202 to enclose the bone-growth inducing substances within the interior cavity. End cap 212 is preferably fabricated from a flexible polymeric material such as polyethylene and is dimensioned to snap into a groove or recess 214 defined in the interior end of cage body 202. End cap 212 includes an axial opening 216 and four equidistally spaced peripheral notches 218.

Referring now to FIGS. 10A–10B, to mount the insertion instrument 100 of FIG. 7A to fusion cage 200, the rounded head 108 of the instrument 100 is positioned within the interior cavity 204 of cage body 202 with diametrically opposed slots 109 (only one is shown) engaging the longitudinal ribs 203 formed within the cage body 202. Once mounted, the cage body 202 is rotated by rotation of the instrument 110. Head 108 may be inserted within interior cavity 204 to a position almost adjacent closed end 206. A spring loaded ball detent system 126 associated with the rounded head 108 frictionally retains the head 108 within cage body 202 as depicted in FIG. 10B. A pair of opposed alignment bars 119 (only one is shown) formed on elongated shaft 102 (FIG. 7A) are positioned in substantial alignment with slots 109 to indicate to the user the orientation of the fusion cage 200.

Application of Instrumentation

The use of the instrumentation kit in conjunction with the insertion of the fusion cage 200 of FIG. 8 into an intervertebral space defined between adjacent lumbar vertebrae will be described. The subsequent description will be particularly focused on an open posterior spinal fusion procedure, however, it is to be appreciated that an anterior approach is contemplated as well.

The intervertebral space is accessed utilizing appropriate retractors, e.g., laminar retractors, dural extractors to expose the posterior vertebral surface. Thereafter, retractor 10 of FIG. 1 with impactor cap 26 mounted thereon is positioned adjacent the intervertebral space. With reference to FIG. 11, retractor arms 20 are inserted within the intervertebral space and the retractor 10 is gently impacted into the space with a mallet. The preferred orientation of retractor arms 20 within the intervertebral space is shown in FIG. 11. As shown, retractor arms 20 are arranged such that first and second supporting surfaces 20a, 20b of each retractor arm respectively engages the opposed vertebral bodies $V_1$, $V_2$. Upon insertion of retractor arms 20, the vertebral bodies $V_1$, $V_2$ are distracted whereby the retractor arms 20 become firmly lodged within the intervertebral space. The arrangement of retractor arms 20 provides a double point contact with each vertebral body (curved end plate), i.e., the first supporting surfaces 20a of retractor arms 20 engage vertebral body $V_1$ at two different locations and in spaced relation. The second supporting surface 20b engage vertebral body $V_2$ in the same manner. Thus, the load exerted by vertebral bodies $V_1$, $V_2$ is distributed at two different locations on retractor 10 and along the entire lengths of the supporting surfaces 20a, 20b thereby firmly and uniformly loading the retractor 10 in the intervertebral space. It is also to be noted that as discussed above, the particular arrangement of the retractor arms 20 within the intervertebral space automatically appropriately aligns retractor 10 with relation to the vertebral bodies $V_1$, $V_2$, i.e., in parallel relation with the vertebral end plates for the subsequent drilling process. Tapered surfaces 24 of retractor arms 20 facilitate entry of the retractor arms 20 into the intervertebral space. The depth of penetration of retractor arms 20 is limited by collar 18 as described above.

Figure 12:
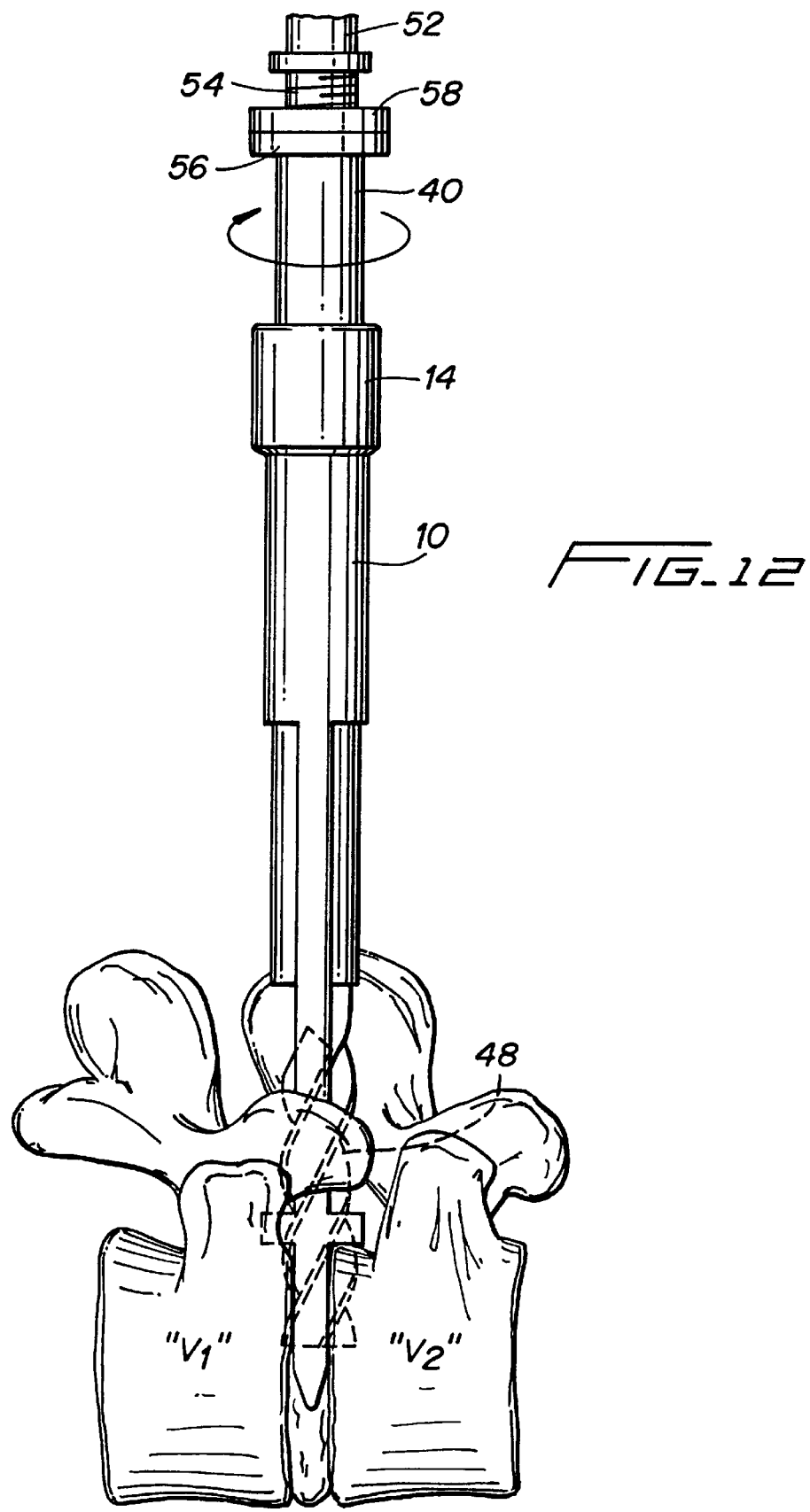
FIG. 12 is a side plan view illustrating insertion of the drilling instrument of FIG. 3 into the retractor to drill a bore within the adjacent vertebrae.

Referring now to FIG. 12, the drilling instrument of FIG. 3A is now used to prepare the disc space and vertebral end plates for insertion of the fusion implant. The cutting depth of drilling instrument 40 is adjusted as desired (i.e., to correspond to the length of the fusion cage) by adjusting the positional collar 56 and securing the collar 56 at the desired position with locking collar 58 as described above. With the T-handle 110 mounted to drilling instrument 40 in the manner described above, the instrument is introduced into retractor 10 and advanced to contact the posterior surface of the vertebral bodies $V_1$, $V_2$. Drill bit 48 communicates with vertebral bodies $V_1$, $V_2$ through slotted opening 22 defined between retractor arms 20 (FIG. 1). Drilling instrument 40 is advanced into the intervertebral space by rotating T-handle 110 in the direction indicated by the directional arrow of FIG. 12 until positional collar 56 engages the proximal end of enlarged head 18 of the retractor 10. This shears the soft tissue and cuts the bone as described above. Depth markings 60 are also monitored to further assist the surgeon. Thereafter, drilling instrument 40 is removed by rotating T-handle 110 in the opposite direction and the instrument 40 is removed from the retractor 10.

When juxtaposed sides of the adjacent vertebral disc have been adequately prepared by drilling the holes and completely removing any remaining soft tissue, tapping instrument 70 of FIG. 5 is selected and attached to the T-handle 110. The purpose of the tapping instrument 70 is to cut the threads into the opposing vertebral endplates. This ensures that the implant will be positioned correctly and will have the correct purchase into the endplates for immediate bone graft material to endplate contact. With reference now to FIG. 13, tapping instrument 70 is inserted into retractor 10 and positioned adjacent the drilled bone. With retractor 10 as a direct guide, T-handle 110 is rotated in the direction of the directional arrow of FIG. 13 while simultaneously applying sufficient downward (distal) pressure on the T-handle 110 to advance the tapping instrument 70 and promote even purchase into the endplates. Upon advancement of the tapping instrument 70, the deburred bone chips collect within conveyance channel 78 of tapping head 74, and are conveyed proximally during rotational movement of the tapping head away from the tapping site. Tapping instrument 70 is advanced into the bone until the desired depth has been achieved which occurs when the distal end of tapping head 74 "bottoms out" on the bone. To further ensure that the tapping instrument 70 reaches the proper depth, the depth markings 82 on tapping instrument 70 are also monitored. Tapping head 74 communicates with vertebral bodies $V_1$, $V_2$ through slotted openings 22 defined between the retractor arms 20. When tapping instrument 70 reaches the appropriate depth, the tapping instrument 70 is rotated via T-handle 110 in an opposite direction to back the instrument out of the bone and the instrument 70 is removed from the retractor 10.

With reference now to FIG. 14, attention is focused on the insertion of the selected fusion implant 200. Cage body 202 is mounted onto insertion instrument in the manner described in connection with FIGS. 10A–10B. With T-handle 110 attached in the manner described above, insertion instrument 100 with mounted cage body 202 is inserted into retractor 10 and the cage body 202 is positioned within the tapped bore by rotating insertion instrument in the direction depicted in FIG. 14. Cage body 202 is advanced until it is completely seated with the bore. The indicator lines on insertion instrument 100 assist the surgeon in determining when the cage is in proper position. Alignment bars 119 indicate to the user the orientation of the cage to assist in ensuring that the perforations 210 are in communication with the vertebral end plates when the cage is finally positioned. Insertion instrument 100 is then removed from retractor 10.

With reference now to FIG. 15, bone growth inducing substances are harvested from, e.g., the illiac crest, and can be packed into a syringe body or tube "s" (as shown in FIG. 15) or other holding device. As depicted in FIG. 16, with the use of forceps "f", the bone growth inducing substances are removed from the syringe "s" and introduced into the cage body 202 until the cage body 202 is completely filled with bone growth inducing substances. The bone growth inducing substances can be lightly impacted to pack the cage.

With reference to FIGS. 17–19, after filling cage body 202, the end cap 212 is mounted to the cage body 202. A preferred instrument 300 for applying end cap 212 includes handle 302 and elongated portion 304 connected to the handle and extending distally therefrom. At the distal end of elongated portion 304 is mounting head or section 306. Mounting head 306 includes distal annular portion 308 with annular nub 310 projecting therefrom and four equidistantly spaced flanges 312. Flanges 312 extend in a radial direction and are preferably spaced about 90° apart as best depicted in FIG. 17. Flanges 312 engage the end cap 312 to limit proximal flexure of the end cap 312 as it is mounted to the cage body 202. In the mounted condition of end cap 212 onto instrument 300, annular nub 310 of the instrument 300 is received within annular opening 216 of end cap 212. Preferably, annular nub 310 and opening 216 are correspondingly dimensioned such that a friction fit between the two components is established.

With reference now to FIG. 20, instrument 300 with mounted end cap 212 is introduced into the operative site and advanced to cage body 202. Thereafter, end cap 212 is mounted to cage body 202 by inserting the end cap 212 within the interior cavity whereby the end cap 212 snaps into correspondingly dimensioned groove 214 (FIG. 9) defined in the cage body 202. During insertion, the peripheral area of end cap 212 is permitted to deform due in part to the flexible characteristics of its material of fabrication and to notches 216, thus enabling the end cap 212 to pass within the cage body 202. It is to be noted that during insertion, flanges 312 of instrument 300 (FIG. 19) prevent any tendency of end cap 212 to rotate relative to the instrument. With end cap 212 mounted within cage body 202, instrument 300 is removed.

Figure 21:
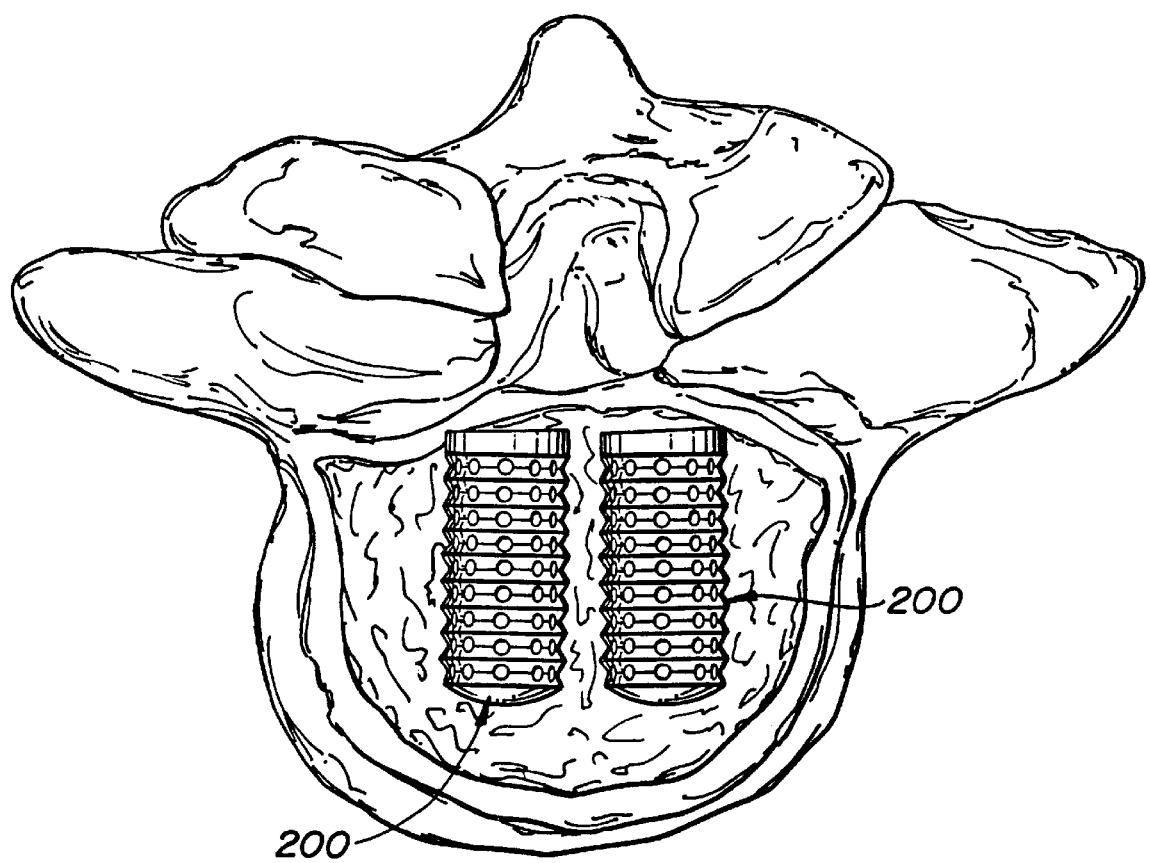
FIG. 21 is an enlarged top view in partial cross-section of a pair of implants positioned into the intervertebral space of a lumbar spinal section.

FIG. 21 illustrates two lateral fusion implants 200 inserted within the lumbar intervertebral space. The second fusion cage 200 is inserted in accordance with the method and instruments previously discussed.

While the above description contains many specifics, these specifics should not be construed as limitations on the scope of the disclosure, but merely as exemplifications of preferred embodiments thereof. For example, the forceps and/or end cap insertion tool can be inserted through the retractor 10 prior to removal of the retractor 10. Those skilled in the art will envision many other possible variations that are within the scope and spirit of the disclosure as defined by the claims appended hereto.

What is claimed is:

1. A method for performing a surgical procedure, comprising the steps of:

providing a surgical retractor including an elongate member defining a longitudinal axis, the elongate member including proximal and distal end portions and defining an opening therethrough to receive instrumentation, the distal end portion configured for insertion at least partially into an intervertebral space between adjacent opposed vertebrae and having two spaced apart retractor arms, each retractor arm including first and second supporting surfaces laterally displaced with respect to each other and to the longitudinal axis;

distracting the adjacent vertebrae by at least partially inserting the retractor arms of the retractor within the intervertebral space whereby the first supporting surface of each retractor arm engages one vertebrae and the second supporting surface of each retractor arm engages the other vertebrae such that the adjacent opposed vertebrae are laterally displaced; and performing the surgical spinal procedure.

2. The method according to claim 1 wherein the step of performing includes introducing surgical instrumentation within the opening of the surgical retractor, the surgical instrumentation being utilized to perform the surgical procedure.

3. The method according to claim 2 wherein the step of performing the surgical procedure includes introducing a fusion implant through the opening in the surgical retractor and between the distracted vertebrae to effect fusion thereof.

4. A method for performing a surgical spinal procedure comprising:

providing a surgical retractor including an elongate member having proximal and distal end portions and defining an opening therethrough to receive instrumentation, the distal end portion configured for insertion at least partially into an intervertebral space between adjacent opposed vertebrae, the elongate member including at least one slot defined in an outer wall surface portion thereof;

distracting the adjacent vertebrae by at least partially inserting the distal end of the retractor within the intervertebral space; and introducing surgical instrumentation within the slot of the elongate member to perform the surgical procedure.

5. A method for fusing adjacent vertebral bodies, comprising the steps of:

a) accessing the intervertebral disc space;

b) providing a retractor including a retractor sleeve having proximal and distal end portions, the distal end portion having opposed retractor arms extending in a general longitudinal direction;

c) positioning the retractor arms within the intervertebral disc space whereby first and second supporting surfaces of each arm contact opposed vertebral bodies;

d) introducing a drill instrument into the sleeve and advancing the drill instrument within the sleeve to the disc space;

e) forming with the drill instrument a bore that penetrates at least partially into each opposed vertebral body;

f) removing the drill instrument from the sleeve; and g) introducing a fusion implant into the bore.

6. The method according to claim 5 further including the steps of:

h) introducing a tap instrument into the sleeve and advancing the tap instrument within the sleeve to the disc space;

i) tapping with the tap instrument a thread within the bore;

j) removing the tap from the retractor sleeve;

k) introducing into the sleeve a fusion cage having a cage body with an external thread; and l) screwing the cage body into the threaded bore.

7. The method according to claim 6 wherein the step of introducing a fusion implant includes introducing a fusion implant having a plurality of openings extending through the cage body.

8. The method according to claim 7 further including the step of filling the cage body with bone-growth inducing substances.

9. The method according to claim 8 further including the step of mounting an end cap to the open end of the cage body to enclose the bone-growth inducing substances within the cage body.

10. The method according to claim 5 wherein the retractor arms define a dimension between the first and second supporting surfaces sufficient to distract the opposed vertebral bodies and wherein the step of positioning the retractor arms includes distracting the opposed vertebral bodies.

11. A surgical retractor instrument comprising an elongated sleeve member including proximal and distal end portions and defining a longitudinal axis, the elongated sleeve member defining a longitudinal passageway for reception of surgical instrumentation, the distal end portion having first and second retractor arms extending in a general longitudinal direction, each retractor arm having first and second opposed supporting surfaces for engaging respective opposed adjacent tissue portions, each retractor arm defining a dimension between the first and second supporting surfaces sufficient to distract the opposed tissue portions upon insertion thereof; and a cap engageable with the proximal end portion of the sleeve member, the cap for receiving the impact of a driving instrument used to engage the retractor instrument with the tissue portions.

12. The surgical retractor according to claim 11 wherein the first and second supporting surfaces of each retractor arm are substantially planar.

13. The surgical retractor according to claim 11 wherein each retractor arm has a tapered end portion for facilitating insertion into the tissue portions.

14. A surgical retractor for use in distracting adjacent vertebrae having an intervertebral space defined therebetween, the retractor comprising:
   an elongate sleeve body having a proximal end and a distal end and the sleeve body having an opening in a side wall portion thereof defining a longitudinal passageway therebetween; and
   first and second retractor arms extending longitudinally from the distal end of the elongate sleeve body, each retractor arm defining a first vertebra supporting surface to contact a first vertebra and a second vertebra supporting surface to contact a second vertebra, the first and second vertebra supporting surfaces of each retractor arm being spaced a predetermined distraction distance at least equal to the height of the intervertebral space defined between the adjacent vertebrae.

15. The surgical retractor according to claim 14 wherein the retractor arms each possess distal tapered portions for facilitating insertion into the intervertebral space.

16. The surgical retractor according to claim 14 wherein the first and second supporting surfaces of each retractor arm are in general parallel relation.

17. A surgical retractor for use in distracting adjacent vertebrae, comprising:
   an elongate body having a proximal end and a distal end and defining a longitudinal passageway therebetween, the elongate body defining a longitudinal axis;
   first and second retractor arms extending longitudinally from the distal end of the elongate body, each retractor arm defining a first vertebra supporting surface and a second vertebra supporting surface, the first and second vertebra supporting surfaces of each retractor arm being spaced a predetermined distance sufficient to contact the adjacent vertebrae to be in supporting engagement therewith, the first and second vertebra support surfaces being in general parallel relation with each other and to the longitudinal axis of the elongate body, and an impactor member mounted adjacent the proximal end of the elongate body and being dimensioned to receive the impact of the driving member utilized to position the first and second retractor arms with respect to the adjacent vertebrae.

18. A surgical retractor for use in distracting adjacent vertebrae, the retractor comprising:
   an elongate sleeve body having a proximal end and a distal end and defining a longitudinal passageway therebetween, the elongate sleeve body including at least one longitudinal opening in an intermediate wall portion; and
   first and second retractor arms extending longitudinally from the distal end of the elongate sleeve body, each retractor arm defining a first vertebra supporting surface to contact a first vertebra and a second vertebra supporting surface to contact a second vertebra, the first and second vertebra supporting surfaces of each retractor arm being spaced thereon at a predetermined distraction distance.

19. A method for performing a surgical procedure comprising:
   providing a surgical retractor including an elongate sleeve member having proximal and distal end portions and defining an opening therethrough to receive instrumentation, the distal end portion configured for insertion at least partially into an intervertebral space between adjacent opposed vertebrae;
   distracting the adjacent vertebrae by at least partially inserting the distal end portion of the sleeve member within the intervertebral space;
   inserting instrumentation through the opening in the surgical retractor; and
   performing the surgical spinal procedure.

20. The method according to claim 19 wherein the step of performing the surgical spinal procedure includes utilizing the instrumentation inserted through the opening in the surgical retractor to perform the surgical spinal procedure.

21. The method according to claim 20 wherein the elongate sleeve member of the surgical retractor defines an axial opening and wherein the step of inserting includes positioning instrumentation through the axial opening to perform the surgical spinal procedure.

22. A method for performing a surgical procedure comprising:
   providing a surgical retractor including an elongate hollow member having proximal and distal end portions, the distal end portion having first and second stationary retractor arms configured for insertion at least partially into an intervertebral space defined between upper and lower opposed vertebrae;
   distracting the adjacent vertebrae to a predetermined distracted position by at least partially inserting the retractor arms within the intervertebral space; and
   performing the surgical spinal procedure.

23. The method according to claim 22 wherein each retractor arm includes first and second opposed supporting surfaces and wherein the step of distracting includes at least partially inserting the retractor arms whereby the first and second supporting surfaces of each retractor arm respectively engage the upper and lower vertebrae.

24. A surgical retractor instrument comprising an elongated sleeve member including proximal and distal end portions and defining a longitudinal axis, the elongated sleeve member defining a longitudinal passageway for reception of surgical instrumentation, the distal end portion having first and second stationary retractor arms extending in a general longitudinal direction, each retractor arm having opposed distracting surfaces, the distracting surfaces of each retractor arm laterally spaced with respect to the longitudinal axis at a predetermined distraction distance sufficient to distract the opposed tissue portions upon insertion thereof the sleeve member including an opening in an outer wall thereof and proximate the distal end portion of the sleeve member.

25. The surgical retractor according to claim 14 wherein the distraction distance of each retractor arm is greater than the height of the intervertebral space.

26. The surgical retractor according to claim 24 wherein the distal end portion is dimensioned for insertion within the intervertebral space defined between adjacent vertebrae and wherein the distraction distance defined between the opposed distracting surfaces of each retractor is at least equal to the height of the intervertebral space.

* * * * *